(12) United States Patent
Thiel et al.

(10) Patent No.: US 8,957,954 B2
(45) Date of Patent: Feb. 17, 2015

(54) RECORDING METHOD FOR OBTAINING AN IMAGE OF AN OBJECT AND RECORDING DEVICE

(75) Inventors: Frank Thiel, Ober-Ramstadt (DE); Peter Fornoff, Reichelsheim (DE); Joachim Pfeiffer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 1146 days.

(21) Appl. No.: 12/793,574

(22) Filed: Jun. 3, 2010

(65) Prior Publication Data

US 2010/0309301 A1    Dec. 9, 2010

Related U.S. Application Data

(63) Continuation of application No. PCT/EP2008/066759, filed on Dec. 4, 2008.

(30) Foreign Application Priority Data

Dec. 4, 2007    (DE) .................. 10 2007 058 590

(51) Int. Cl.
*H04N 7/18* (2006.01)
*H04N 9/47* (2006.01)
*G01B 11/25* (2006.01)
*A61B 5/00* (2006.01)
*A61C 13/00* (2006.01)
*A61B 5/103* (2006.01)

(52) U.S. Cl.
CPC ............. *G01B 11/25* (2013.01); *A61B 5/0088* (2013.01); *A61C 13/0004* (2013.01); *G01B 11/2527* (2013.01); *A61B 5/0077* (2013.01); *A61B 5/103* (2013.01)

USPC ............................................... 348/77

(58) Field of Classification Search
CPC .... A61B 5/0077; A61B 5/0088; A61B 5/103; A61C 13/0004; G01B 11/25; G01B 11/2527
USPC .................. 348/77; 382/141, 154, 173
See application file for complete search history.

(56) References Cited

U.S. PATENT DOCUMENTS

| | | | |
|---|---|---|---|
| 4,837,732 A | 6/1989 | Brandestini et al. | 364/413.28 |
| 5,604,817 A * | 2/1997 | Massen et al. | 382/120 |
| 5,986,745 A | 11/1999 | Hermary et al. | 356/3.03 |
| 6,369,899 B1 | 4/2002 | Hamada | 356/603 |
| 7,342,668 B2 * | 3/2008 | Quadling et al. | 356/603 |
| 2003/0026475 A1 * | 2/2003 | Yahashi et al. | 382/154 |
| 2004/0151360 A1 | 8/2004 | Pirard et al. | 382/141 |
| 2004/0151369 A1 | 8/2004 | Schwotzer | 382/154 |
| 2005/0099638 A1 | 5/2005 | Quadling et al. | 356/603 |
| 2007/0187581 A1 * | 8/2007 | Ohmura et al. | 250/231.13 |

(Continued)

FOREIGN PATENT DOCUMENTS

| | | |
|---|---|---|
| DE | 24 10 947 A1 | 9/1975 |
| DE | 103 04 111 A1 | 10/2004 |

(Continued)

*Primary Examiner* — Anner Holder
(74) *Attorney, Agent, or Firm* — Fitzpatrick, Cella, Harper & Scinto

(57) ABSTRACT

A method for recording an image of an object includes projecting a strip pattern onto the object, recording the projected strip pattern as raw image data using a camera, and calculating an image of the object from the raw image data. A strip pattern having a duty cycle of less than 1 can be used to increase measuring precision during measurement of a translucent object, and can eliminate a need for additional contrast agents for a recording of the object.

17 Claims, 5 Drawing Sheets

(56) References Cited

U.S. PATENT DOCUMENTS

| | | | |
|---|---|---|---|
| 2009/0096783 A1 | 4/2009 | Shpunt et al. | 345/419 |
| 2009/0221874 A1 | 9/2009 | Vinther et al. | 600/178 |
| 2010/0046005 A1* | 2/2010 | Kalkowski et al. | 356/604 |

FOREIGN PATENT DOCUMENTS

| | | |
|---|---|---|
| DE | 103 58 544 A1 | 7/2005 |
| JP | 2000-146543 A | 5/2000 |
| JP | 2000-292135 A | 10/2000 |
| JP | 2002-257528 A | 9/2002 |
| JP | 2005-172459 A | 6/2005 |
| WO | WO 2005/027770 A2 | 3/2005 |
| WO | 2007/059780 A1 | 5/2007 |
| WO | WO 2007/059780 A1 | 5/2007 |
| WO | WO 2007/105215 A2 | 9/2007 |

* cited by examiner

RECORDING METHOD FOR OBTAINING AN IMAGE OF AN OBJECT AND RECORDING DEVICE

CROSS REFERENCE TO RELATED APPLICATIONS

The present application is a continuation of International Patent Application No. PCT/EP2008/066759, filed Dec. 4, 2008, which claims priority to German Patent Application No. 10 2007 058 590.1, filed Dec. 4, 2007. The entire disclosure of each prior application is incorporated by reference herein.

BACKGROUND OF THE INVENTION

The invention relates to a method for creating an image of an object to be imaged, particularly for dental purposes, comprising the method steps: projecting a striped pattern onto the object to be imaged, recording the projected striped pattern as a raw image with a camera, and computing an image of the object to be imaged from the raw image. The image can, in particular, be a height image or an intensity image of a prepared tooth or an impression thereof.

The invention further relates to a device for executing this method.

PRIOR ART

For direct optical three-dimensional measurement of objects, for example, to obtain digital design data for computer-controlled production, the principle of triangulation can be used, in which a single stripe of light or a striped pattern of parallel stripes is projected by projecting means onto the object to be scanned, and the projected image is recorded at a parallax angle by a two-dimensional camera. By reason of the surface structure of the objects to be imaged the run of a stripe no longer appears to be straight, but instead is curved and offset from the straight course. The surface structure of the objects being imaged can then be concluded from the orientation of the stripes of light.

In order to increase the accuracy, use can be made of the so-called phase shifting triangulation method. A plurality of raw images in the same imaging area at various positions of the phasing of a stripe grid is successively produced and a phase-related image is computed therefrom. A height image of the object to be imaged, or alternatively a high-contrast image thereof, can then be computed, by means of calibration data, from the phase-related image. The height image can be in the form of a 3D data set. In order to attain precise computation of the images, striped patterns with a sinusoidal intensity distribution are generally used. The triangulation method and also the phase shifting triangulation method are more precisely described in, for example, U.S. Pat. No. 4,837,732.

Three-dimensional scanning, more particularly of translucent objects such as teeth, by means of the stripe projection method, produces raw data which are typically of poorer quality than when scanning fully opaque objects. This means, inter alia, that the raw data obtained on translucent objects have a lower signal amplitude and consequently the three-dimensional data obtained therefrom are of poorer quality. On account of the light that penetrates the object and is back-scattered by diverse mechanisms, there is formed, when imaging translucent objects, a strong noise signal which can provide no information or only erroneous information regarding the three-dimensional geometry of the surface of the object.

This undesirable, effect resulting from the translucency of the surface, on the three-dimensional surface information contained in raw images decreases with increasing grid period of the stripe grid pattern used for the stripe projection. However, an increase in the grid constants fundamentally results in a reduction of the measuring accuracy.

For this reason, a contrast medium is nowadays typically used. This contrast medium is frequently a powder, which is applied to the object to be scanned and ensures that a major portion of the incident light is reflected by the surface of the object, whereby a higher signal amplitude can be obtained. However, the application of a contrast medium involves higher expenditure and may reduce measuring accuracy when the layer is uneven. The undesirable noise signals occur with all translucent objects or, more generally speaking, with all objects in which backscattering takes place in the interior thereof.

DE 103 04 111 A1 discloses an approach for increasing the accuracy of data obtained by the phase shifting triangulation method, which approach involves the division of raw images into groups, from each of which a phase-related image is produced. The phase-related images thus obtained are averaged in order to suppress disturbances derived from the periodicity of the grid. However, this approach is not purposeful as regards the problem of increased backscattering within an object to be imaged.

It is an object of the invention, as characterized in the claims, to provide a method of the type mentioned above for imaging an object to be imaged and a device for imaging an object to be imaged in which adequate measuring accuracy can be acquired without the use of a contrast medium.

SUMMARY OF THE INVENTION

This object of the invention is achieved, according to the invention, by the method defined in claim 1 and the recording device defined in claim 10. Advantageous embodiments of the invention are the subject matter of the subordinate claims.

The invention improves on the prior art in that, in order to increase the measuring accuracy, the striped pattern projected onto the object to be imaged has a mark-space ratio of less than 1. In this way, raw images for the computation of height images or intensity images are provided, and, depending on the method used, just one raw image may be sufficient.

The term "mark-space ratio" is taken below to mean the ratio of illuminated or bright areas to non-illuminated or dark areas in the resulting projected stripe patterns. In the case of a mark-space ratio of less than 1, the projected stripe patterns produce a surface having more dark areas than bright areas.

The invention is based on the fact that when use is made of a striped pattern with a mark-space ratio of less than 1, the original pattern is not so broadened or faded. For a given grid constant, the use of a striped pattern having a mark-space ratio of less than 1 leads to a greater signal amplitude than a conventionally used sinusoidal striped pattern having a mark-space ratio equal to 1 or a striped pattern having a mark-space ratio greater than 1. Undesirable noise signals are thus substantially reduced, especially in the case of translucent surfaces.

The lower the mark-space ratio, the greater the ascertainable positive effect. A reduction in the intensity of the light impinging on the object to be imaged and reflected therefrom as occurs with very small mark-space ratios can be compensated for by an appropriate prolongation of the exposure time during image creation.

In a preferred embodiment of the method, projection of the striped pattern and imaging of the projected striped pattern can be carried out at constant alignment of the camera relative to the object to be imaged and at a plurality of different positions of the phasing of the striped pattern and the image can be computed from the plurality of mutually phase-shifted camera raw images.

Thus, in order to increase accuracy, a plurality of raw images are successively produced at different positions of the phasing of the grid, from which raw images a phase-related image is computed. From the phase-related image there can then be computed a height image of the object to be imaged, optionally with the aid of calibration data. Alternatively, a high-contrast image can be computed from the raw images.

Particularly suitable, especially in the case of the phase shifting triangulation method, are periodic striped patterns. With regard to periodic striped patterns, a mark-space ratio of less than 1 can be achieved, inter alia, when within a period the width of the area which is illuminated with an intensity of more than 50% of the maximum intensity of radiation is smaller than the width of the area illuminated with an intensity of less than 50% of the maximum intensity of radiation. The first-named area is equivalent to a stripe of light and the second-named area to a stripe of darkness.

Preferably, in the case of periodic striped patterns, the area within a period which is illuminated with an intensity of less than 30% of the maximum intensity of radiation is greater than the area which is illuminated with an intensity of 50% or more of the maximum intensity of radiation.

More preferably, with regard to achieving a high measuring accuracy, the area within a period which is illuminated with an intensity of less than 20% of the maximum intensity of radiation is greater than the area illuminated with an intensity of more than 50% of the maximum intensity of radiation. The distribution of the bright and dark stripes of the striped pattern may, for example, be a rectangular distribution. In special embodiments of the method, a striped pattern is projected whose intensity distribution corresponds to a Gaussian distribution or a sinusoidal distribution including at least one further harmonic term. Such distributions have the advantage over, for example, a rectangular distribution, that when use is made of the phase shifting triangulation method, in which a plurality of raw images are created successively at various positions of the phasing of the striped pattern, the formulas used for conventional sinusoidal distributions may also be used for the evaluation of the raw data to form height or contrast images.

In particular, in connection with the use of the phase shifting triangulation method, it has been found that it is advantageous to determine, for evaluation and computation of the image produced from each raw image, at least one measuring point which corresponds, in all raw images, to a certain position in the plane of projection, and to compare the measured intensities at said point with the irradiated intensity distribution within the scope of a corrective computation, in order to determine the phasing of the intensity distribution at the at least one measuring point and to conclude therefrom the height of the object to be imaged at this position in the plane of projection. Such numerical evaluation of the data permits basically precise evaluation of the data, particularly in the case of stripe distributions for which no closed formulas for evaluation are available.

A recording device of the invention suitable for carrying out the method described above includes a projecting means for projecting a striped pattern onto the object to be imaged, a camera for creating a raw image of the projected striped pattern, and means for computing an image of the object to be imaged from the at least one raw image, the projecting means being designed such that they project a striped pattern having a mark-space ratio of less than 1.

This may be achieved, for example, by the provision of projecting means having an appropriate grid or having an appropriate projected pattern of which the width of the translucent areas is smaller than the width of the opaque areas by such an amount, that in the plane of projection at the object to be imaged the brighter areas are narrower than the darker areas.

Advantageously, the striped pattern to be projected onto the object to be imaged is variable in terms of its position of the phasing, in order that a plurality of raw images at various phasings can be provided within the same imaging area.

For example, a driving system for the grid to be provided according to the invention can be provided which, on account of appropriate distribution of velocities, leads to a projected striped image having a mark-space ratio of less than 1. Alternatively, the two measures can be combined.

Finally, a desired projected pattern can alternatively be achieved by a punctiform illumination of the object to be imaged when the point is passed at such a speed across the surface to be scanned and the exposure time for the raw image is sufficiently long for a projected pattern to be formed in the raw image. Such projecting devices are known from the prior art.

BRIEF DESCRIPTION OF THE DRAWINGS

The invention is explained in greater detail below with reference to an exemplary embodiment illustrated in the drawings. Only those elements are illustrated that are essential for comprehension of the invention. In the drawings.

DESCRIPTION OF EMBODIMENTS

Figure 1A:
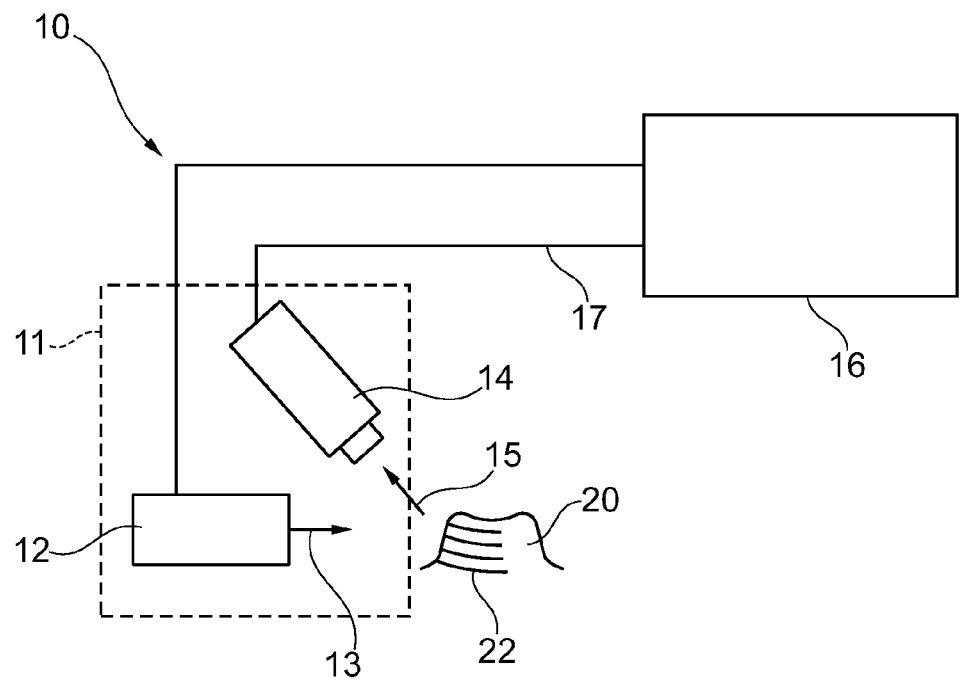
FIGS. 1a, 1b are diagrammatic illustrations of a recording device operating on the principle of phase shifting triangulation.

FIG. 1a is a diagrammatic view of a recording device designated generally by reference numeral 10 and operating on the principle of phase shifting triangulation. The projecting means 12 produces a grid of light with parallel stripes, which is projected onto an object to be imaged, which in this exemplary embodiment is a dental prosthetic item 20. By reason of the three-dimensional surface structure of the tooth 20, the lines of light in the grid on the tooth appear as curved lines at irregular intervals. The image 22 projected via the projected beam 13 is captured at a parallax angle with a two-dimensional camera 14 disposed in the monitoring beam 15 and sent, for evaluation, to an evaluation unit 16. The projecting means 12 and camera 14 may be combined to form a structural unit 11.

Figure 1B:
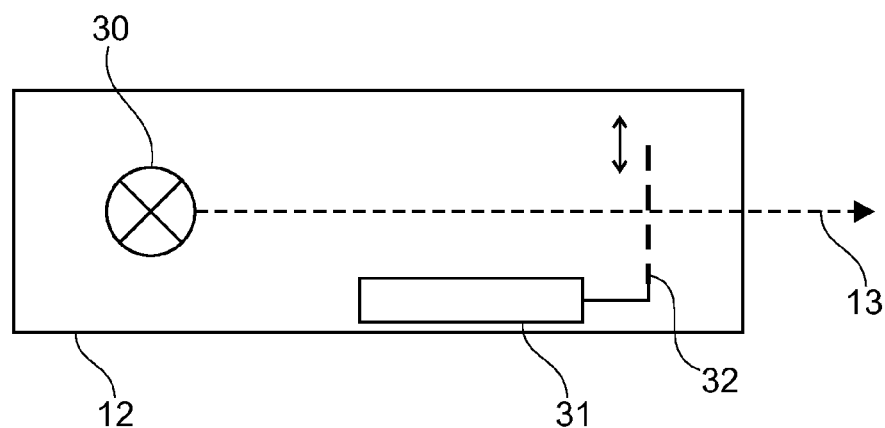

FIG. 1b shows the diagrammatic structure of the projecting means 12 in greater detail. A light source 30 produces a light beam which passes through an optical grid 32. The grid 32 is such that a striped pattern is projected onto the dental prosthetic item 20 in which the dark areas are larger than the bright areas. For this purpose the grid 32 is designed in the present example such that in the plane of projection on the dental prosthetic item 20 there is formed a striped pattern with the desired intensity distribution showing a mark-space ratio of less than 1. The drive 31 can be used to set different phase shifts of the projected striped pattern within the scope of the phase shifting triangulation method.

The captured images can be read out via a cable 17 to the evaluation unit 16 and stored. A height image of the dental prosthetic item 20 can be computed by means of the evaluation unit 16 from at least one raw image, which height image can then be stored as a 3D data set for example. The evaluation unit 16 can for this purpose include components of a conventional computer. Following the measuring procedure there is present in a memory of the evaluation unit 16 connected to the camera 14 a digital three-dimensional data model of the dental prosthetic item 20, which can be displayed as an image, more particularly as a high-contrast image, or can serve as a basis for the computer-controlled design, production, or quality control, of a dental prosthesis.

Figure 2A:
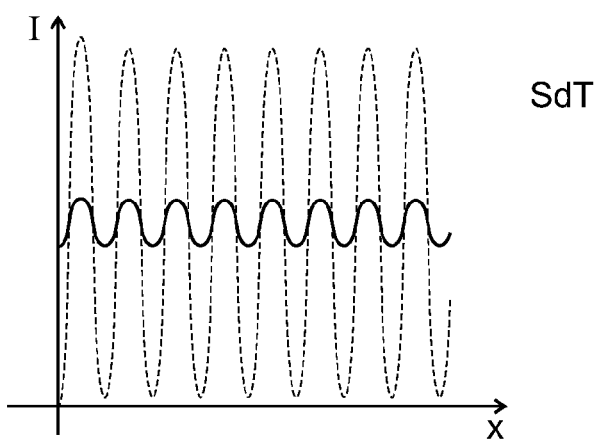
FIGS. 2a to 2c show comparisons of various projected intensity distributions with the respective intensity distributions as measured.
Figure 2B:
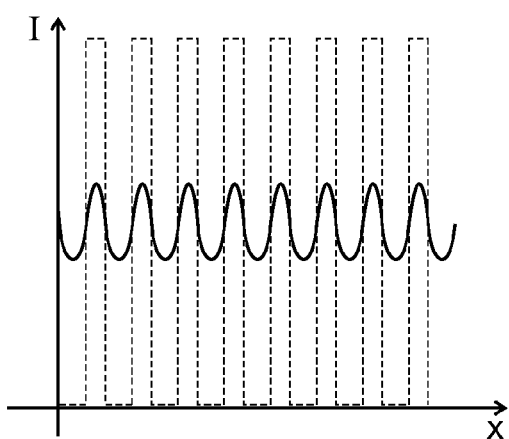
Figure 2C:
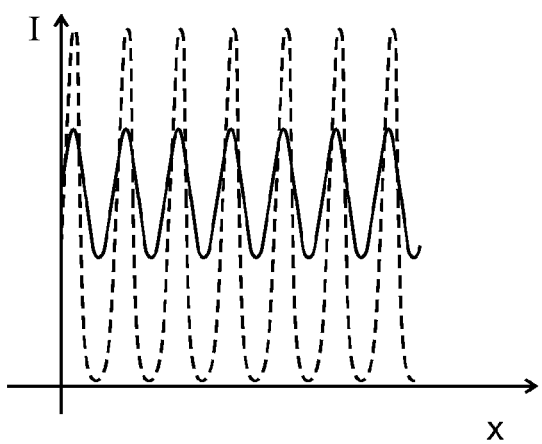

FIGS. 2a to 2c show various intensity distributions such as are projected onto the object to be imaged. The distribution in FIG. 2 is a conventional sinusoidal distribution (dashed), while in FIG. 2b it is a rectangular distribution (dotted) and in FIG. 2c a striped pattern with Gaussian distribution (dashed).

All three striped patterns have the same grid period and the same maximum intensity, but they differ in their mark-space ratios. In the case of a sinusoidal distribution, there is the same number of illuminated or bright areas as there are non-illuminated or dark areas (FIG. 2a, mark-space ratio=1), while in the case of the rectangular distributions and the Gaussian distribution, the widths of the bright or illuminated areas are, according to the invention, such that they are smaller than the non-illuminated or dark regions (FIG. 2b,c, mark-space ratio less than 1).

A continuous line diagrammatically illustrates each of the signals measured at a parallax angle following reflection by the object to be imaged. It has been found that for otherwise identical conditions the measured signal of the measured intensities at a mark-space ratio of less than 1 is greater than at a mark-space ratio equal to 1, so that at a mark-space ratio of less than 1 there is improved measuring accuracy. Comparison of the rectangular distribution with the Gaussian distribution, both of which have the same half-width value, shows that further reduction of the intensely illuminated area in favor of the dark area produces, for the Gaussian distribution compared with the rectangular distribution, a further reduction in the mark-space ratio and thus a higher signal amplitude of the measured intensity.

While the typically valid forms for a sinusoidal distribution are not useful in the case of a rectangular distribution for evaluating the phase-related or height information of the signal shape or would lead to severe systematic errors, this is not the case with grids having Gaussian intensity distributions. In the case of Gaussian intensity distributions, the systematic error is negligible with respect to the required measuring accuracy for, say, the production of an optical impression of teeth or other objects.

Particular preference is given to a mark-space ratio of 1:3 for a Gaussian intensity distribution, which is achieved when the half-width value equals one quarter of the period of the striped pattern.

Figure 3A:
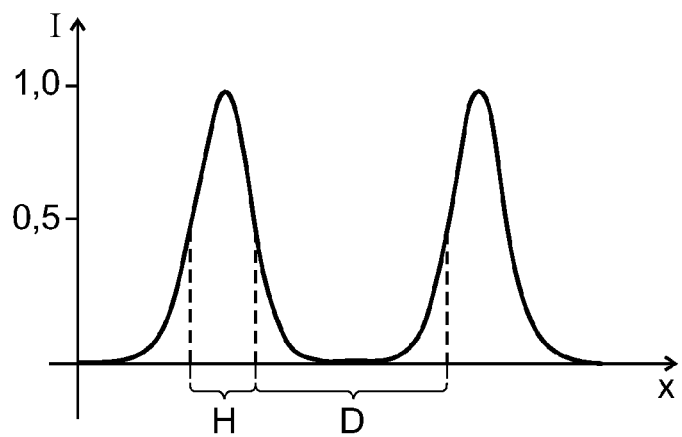
FIGS. 3a to 3c show a striped pattern of the invention having a Gaussian intensity distribution and a mark-space ratio of less than 1.
Figure 3B:
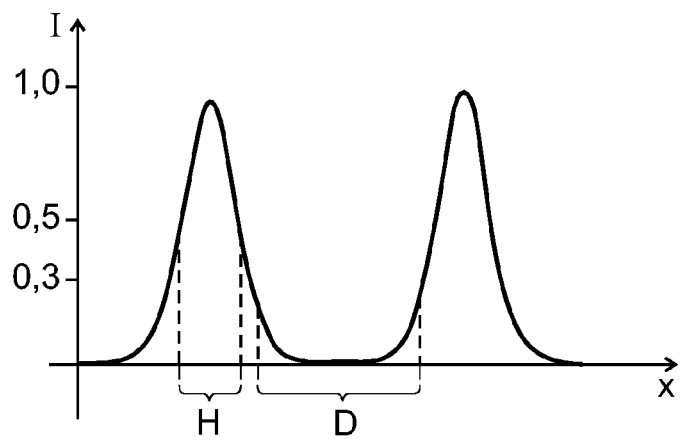
Figure 3C:
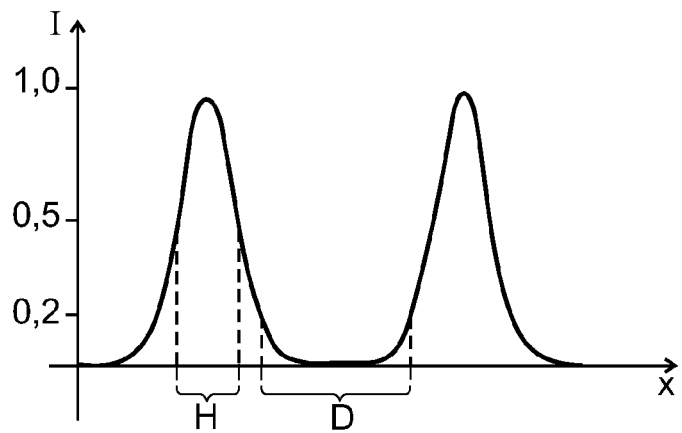

A periodic Gaussian intensity distribution having a mark-space ratio of 1:3 is shown in FIGS. 3a to 3c. For the purpose of illustrating the concept of the mark-space ratio, one way of determining the mark-space ratio quantitatively is shown below. For this purpose there is determined, within a period, the width H of the area that is illuminated with an intensity greater than or equal to 50% of the maximum intensity. In addition, the width D of the area is determined which is illuminated with less than 50% (FIG. 3a), less than 30% (FIG. 3b) or less than 20% (FIG. 3c) of the maximum intensity. In order to improve the measuring accuracy compared with conventional striped patterns having a sinusoidal distribution and a mark-space ratio equal to 1, the dark area should always be broader than the bright area. The measuring accuracy can be particularly well increased when not only the area illuminated with an intensity of less than 50% is broader than the bright area but also the area illuminated with an intensity of less than 30% or even less than 20% of the maximum intensity.

Reference is made to the fact that in the case of very small mark-space ratios, the exposure time may have to be prolonged in order to obtain a sufficient total intensity of the measured signal. Particularly small mark-space ratios are therefore preferably used for applications in which the object to be imaged is scanned with the aid of a stationary recording device. When use is made of stationary recording devices, dental prosthetic items can be scanned for monitoring purposes during or after fabrication thereof.

In the case of applications in which a mobile recording device is used, such as when a tooth is scanned by means of an intraoral camera, higher mark-space ratios are rather preferred in order to obviate the judder effect in the raw images caused by hand trembling while holding the recording device.

Instead of the striped pattern having a Gaussian intensity distribution as illustrated in FIGS. 3a to 3c, it is possible to use other grid patterns. Special preference is given to intensity distributions in which the striped pattern is clearly defined in the region of the levels of intensity differing from zero.

Figure 4A:
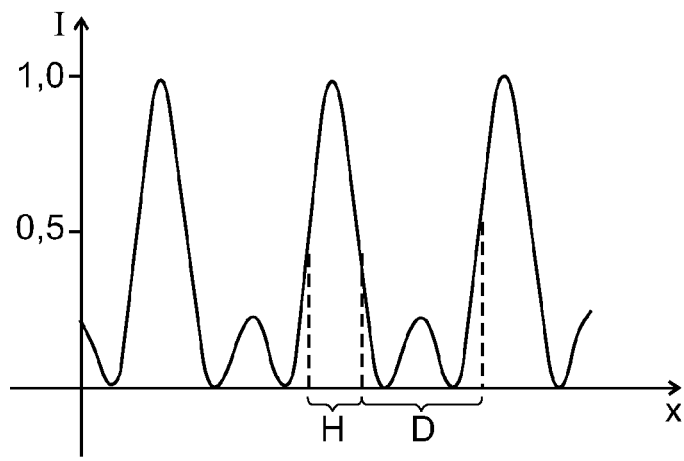
FIGS. 4a to 4c show a striped pattern of the invention with a distribution corresponding to the sinusoidal function including the first harmonic term and having a mark-space ratio of less than 1.
Figure 4B:
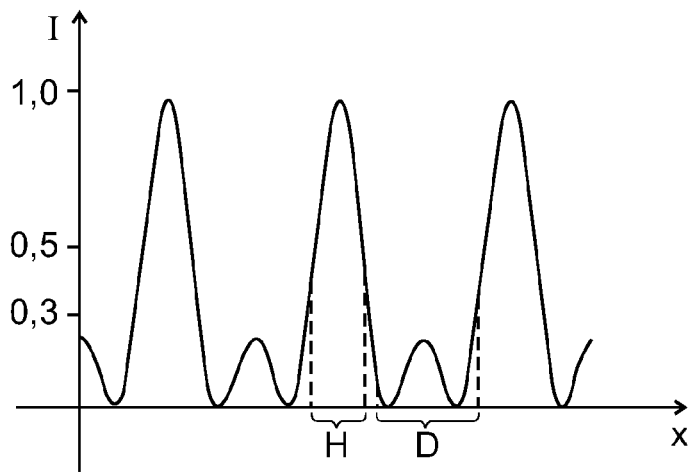
Figure 4C:
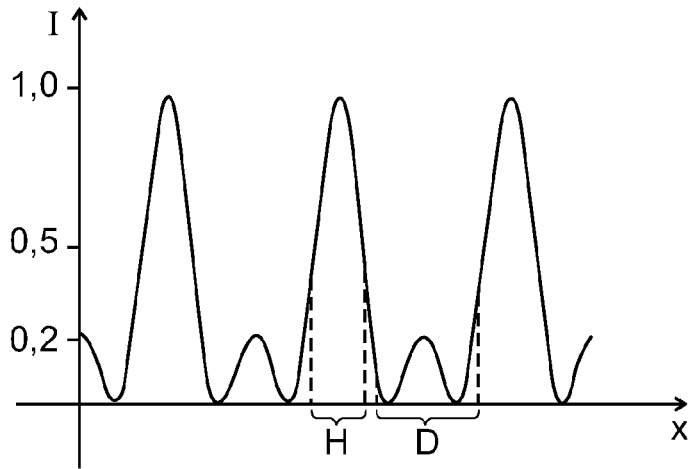

Another striped pattern of the invention is illustrated in FIGS. 4a to 4c. This intensity distribution corresponds to a sinusoidal distribution including the first harmonic term, i.e. a function sin(x)+sin(2x). This striped pattern is particularly suitable for use within the scope of the phase shifting triangulation method. For this intensity distribution, the phase-related or three-dimensional information can be precisely computed with the aid of the pixel-wise evaluation of the tangent formula well known from the literature. As in FIGS. 3a to 3c, the widths of the bright or dark areas in a period have also been characterized in FIGS. 4a to 4c. In addition, distributions having one other or a plurality of harmonic terms are suitable for acquiring sufficient measuring accuracy on translucent objects to be imaged without the use of a contrast medium.

The use of one of the described advantageous intensity distributions of the striped pattern increases the evaluation-relevant signal amplitude in the raw images, especially in the case of objects to be imaged which have translucent surfaces.

Depending on the accuracy requirements of the application, various evaluations are possible with which the phase-related or three-dimensional information can be generated from the one or more recorded raw images: It is possible to carry out an evaluation in the sense of a passive triangulation in which a raw image is recorded. It is also possible to use the phase shifting triangulation method and in the case of suitable intensity distributions to apply the standard formulas known for sinusoidal distributions.

Figure 5:
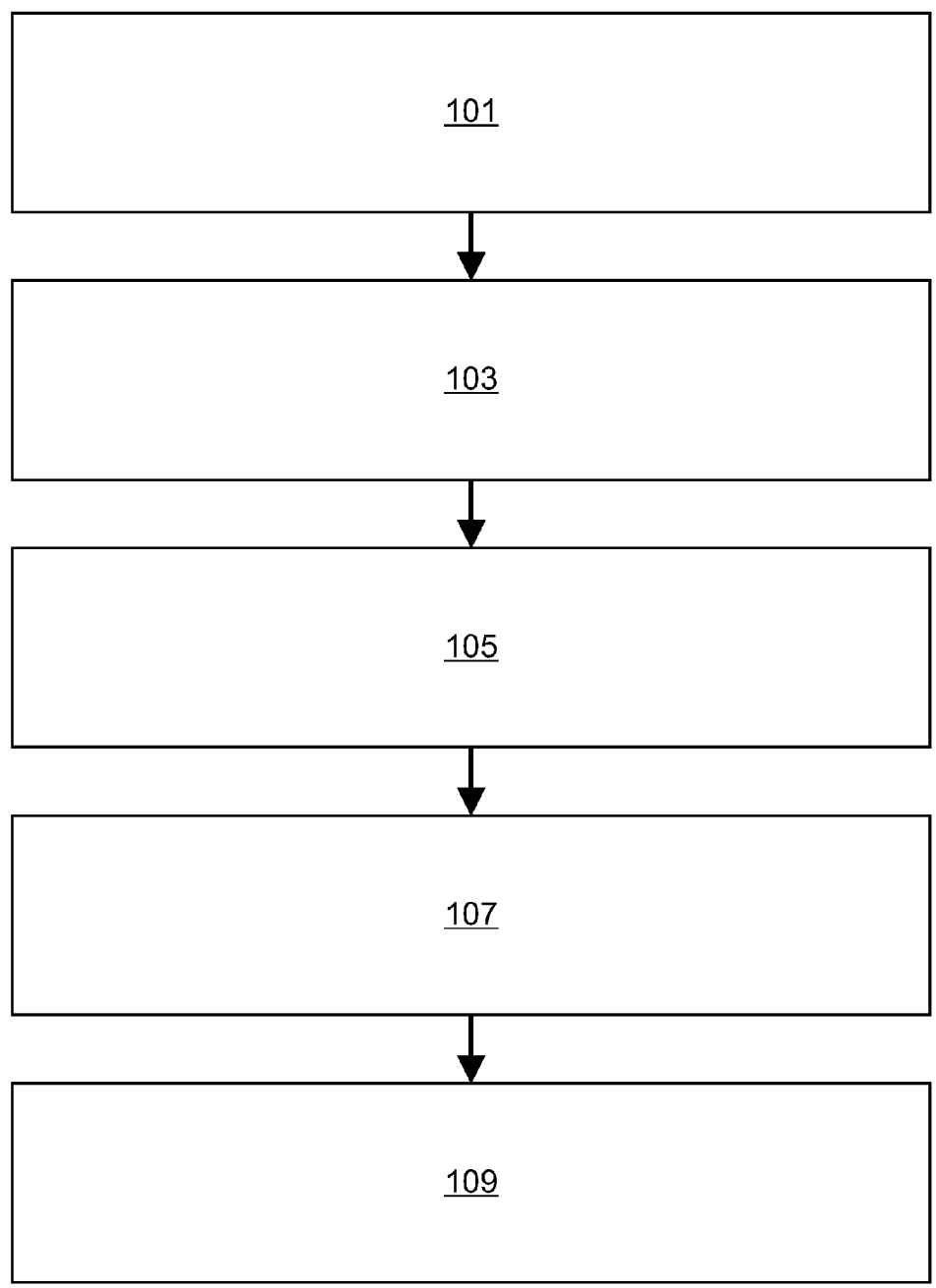
FIG. 5 is a flow chart of an embodiment of the recording method of the invention using the phase shifting triangulation method.

Likewise a numerical approach to evaluation can be used in the phase shifting triangulation method. An example embodiment is illustrated in FIG. 5. First of all, at least two raw images of an object to be imaged can be created at different phase shifts of the striped pattern having a mark-space ratio of less than 1 in the plane of projection on the object to be imaged with the aid of a two-dimensional detector, the alignment of the detector or of a camera toward the object to be imaged being the same when creating the two raw images (step 101). For evaluation, at least one measuring point is selected which corresponds in all raw images to a specific position in the plane of projection (step 103). A corrective computation is carried out for this at least one measuring point, at which the intensity measured in each of the individual raw images is compared with the projected intensity distribution (step 105). From the result of the corrective computation it is possible to ascertain the phasing of the intensity distribution at the position in the plane of projection corresponding to the at least one measuring point (step 107). From the phasing at the position in the plane of projection of the known projected intensity distribution having a mark-space ratio of less than 1, it is possible to determine the height of the object to be imaged at this position (step 109). By "height" is meant the coordinate at right angles to the plane of projection, i.e. substantially in the direction of the projected beam. It is a measure of the distance of the surface of the object being imaged from the plane of projection.

Instead of a striped pattern showing a continuous course of the brightness of the stripes it is possible to used striped patterns having discontinuous, that is to say, resolved or broken stripes, as known, for example, from the prior art as stroke width-modulated grids.

The invention claimed is:

1. A method for creating an image of an object, comprising the steps of:
   a) projecting light through an optical grid having a Gaussian intensity distribution and toward an object to create a striped pattern on the object, said striped pattern having an area-specific mark-space ratio less than 1 and an intensity distribution corresponding to a Gaussian distribution;
   b) recording the striped pattern projected onto the object with a camera to form a raw image; and
   c) computing an image of said object from said raw image.

2. The method according to claim 1, wherein steps a) and b) are carried out at constant alignment of the camera relative to said object and at a plurality of different positions of a phasing of the striped pattern, and the image is computed from a plurality of mutually phase-shifted raw images.

3. The method according to claim 1, wherein within one period of the periodic striped pattern, a width of an area illuminated with an intensity greater than or equal to 50% of a maximum intensity of radiation is smaller than a width of an area illuminated with an intensity of less than 50% of the maximum intensity of radiation.

4. The method according to claim 1, wherein within one period of the periodic striped pattern, a width of an area illuminated with an intensity greater than or equal to 50% of a maximum intensity of radiation is smaller than a width of an area illuminated with an intensity of less than 30% of the maximum intensity of radiation.

5. The method according to claim 4, wherein within one period of the periodic striped pattern, a width of said area illuminated with an intensity greater than or equal to 50% of a maximum intensity of radiation is smaller than a width of an area illuminated with an intensity of less than 20% of the maximum intensity of radiation.

6. The method according to claim 1, wherein the area-specific mark-space ratio is 1:3, and a half-width value is equal to one quarter of a period of the striped pattern.

7. The method according to claim 2, wherein each of the raw images is used to produce the image, and computation of the image includes determining at least one measuring point that corresponds, in all of the raw images, to a certain position in a plane of projection, and measured intensities at said at least one measuring point are compared with an irradiated intensity distribution within a scope of a corrective computation, to determine a phasing at the at least one measuring point and a height of the object at the certain position in the plane of projection.

8. A recording device for creating an image of an object, comprising:
   a projector that projects a striped pattern onto said object, the striped pattern having an area-specific mark-space ratio of less than 1 and an intensity distribution corresponding to a Gaussian distribution, the projector including an optical grid having a Gaussian intensity distribution for generating the striped pattern;
   a camera that captures the projected striped pattern as a raw image; and
   a computing device that computes a height image of said object from at least one raw image.

9. The recording device according to claim 8, wherein a position of a phasing of the striped pattern projected onto said object is variable.

10. A method for creating an image of an object, comprising steps of:
    a) projecting light through an optical grid having a sinusoidal intensity distribution that includes at least one harmonic term toward an object to create a striped pattern on the object to be imaged, said striped pattern having an area-specific mark-space ratio of less than 1 and an intensity distribution corresponding to a sinusoidal distribution that includes at least one harmonic term;
    b) recording the striped pattern projected onto the object with a camera to form raw image; and
    c) computing an image of said object from said raw image.

11. A recording device that creates an image of an object, comprising:
    a projector that projects a striped pattern onto said object, the striped pattern having an area-specific mark-space ratio of less than 1 and an intensity distribution corresponding to a sinusoidal distribution including at least one harmonic term, the projector including an optical grid having a sinusoidal intensity distribution including at least one harmonic term for generating the striped pattern;
    a camera that captures the projected striped pattern as a raw image; and
    a computing device that computes a height image of said object from at least one raw image.

12. The method according to claim 10, wherein within one period of the periodic striped pattern, a width of an area illuminated with an intensity greater than or equal to 50% of a maximum intensity of radiation is smaller than a width of an area illuminated with an intensity of less than 50% of the maximum intensity of radiation.

13. The method according to claim 12, wherein within one period of the periodic striped pattern, a width of an area illuminated with an intensity greater than or equal to 50% of a maximum intensity of radiation is smaller than a width of an area illuminated with an intensity of less than 30% of the maximum intensity of radiation.

14. The method according to claim 13, wherein within one period of the periodic striped pattern, a width of said area illuminated with an intensity greater than or equal to 50% of a maximum intensity of radiation is smaller than a width of an area illuminated with an intensity of less than 20% of the maximum intensity of radiation.

15. The method according to claim 12, wherein each of the raw images is used to produce the image, and computation of the image includes determining at least one measuring point that corresponds, in all of the raw images, to a certain position in a plane of projection, and measured intensities at said at least one measuring point are compared with an irradiated intensity distribution within a scope of a corrective computation, to determine a phasing at the at least one measuring point and a height of the object at the certain position in the plane of projection.

16. The method according to claim 13, wherein each of the raw images is used to produce the image, and computation of the image includes determining at least one measuring point that corresponds, in all of the raw images, to a certain position in a plane of projection, and measured intensities at said at least one measuring point are compared with an irradiated intensity distribution within a scope of a corrective computation, to determine a phasing at the at least one measuring point and a height of the object at the certain position in the plane of projection.

17. The method according to claim 14, wherein each of the raw images is used to produce the image, and computation of the image includes determining at least one measuring point that corresponds, in all of the raw images, to a certain position in a plane of projection, and measured intensities at said at least one measuring point are compared with an irradiated intensity distribution within a scope of a corrective computation, to determine a phasing at the at least one measuring point and a height of the object at the certain position in the plane of projection.

* * * * *